United States Patent
Glenn et al.

(10) Patent No.: US 9,703,407 B1
(45) Date of Patent: Jul. 11, 2017

(54) MOTION RESTRICTION AND MEASUREMENT FOR SELF-ADMINISTERED COGNITIVE TESTS

(71) Applicant: The Cognitive Healthcare Company, San Francisco, CA (US)

(72) Inventors: Shenly Glenn, San Francisco, CA (US); Joel Mefford, Benicia, CA (US); Angele Pieters, Palo Alto, CA (US)

(73) Assignee: The Cognitive Healthcare Company, San Francisco, CA (US)

( * ) Notice: Subject to any disclaimer, the term of this patent is extended or adjusted under 35 U.S.C. 154(b) by 87 days.

(21) Appl. No.: 14/882,391

(22) Filed: Oct. 13, 2015

Related U.S. Application Data

(60) Provisional application No. 62/063,000, filed on Oct. 13, 2014.

(51) Int. Cl.
| | | |
|---|---|---|
| *G06F 3/041* | (2006.01) | |
| *G06F 3/0488* | (2013.01) | |
| *G06F 19/00* | (2011.01) | |
| *G09B 7/02* | (2006.01) | |
| *A61B 5/11* | (2006.01) | |
| *A61B 5/16* | (2006.01) | |
| *A61B 5/00* | (2006.01) | |

(52) U.S. Cl.
CPC ............ *G06F 3/041* (2013.01); *A61B 5/1124* (2013.01); *A61B 5/16* (2013.01); *A61B 5/7475* (2013.01); *G06F 3/0416* (2013.01); *G06F 3/0488* (2013.01); *G06F 19/363* (2013.01); *G09B 7/02* (2013.01); *G06F 2203/04104* (2013.01); *G06F 2203/04808* (2013.01)

(58) Field of Classification Search
CPC ......... G06F 3/041; G06F 19/363; G06F 19/70
See application file for complete search history.

(56) References Cited

U.S. PATENT DOCUMENTS

| | | | |
|---|---|---|---|
| 2012/0004932 A1* | 1/2012 | Sorkey ................... | G06Q 10/06 705/3 |
| 2013/0345524 A1* | 12/2013 | Meyer ................... | G06F 19/363 600/301 |
| 2014/0249447 A1* | 9/2014 | Sereno ................ | A61B 5/6898 600/558 |

* cited by examiner

*Primary Examiner* — Kevin M Nguyen
(74) *Attorney, Agent, or Firm* — Fenwick & West LLP

(57) ABSTRACT

A client device is configured with a test administration application for conducting self-administered tests. The user interface of the test administration application includes motion restriction regions for restricting certain body parts from moving or certain body motions during the entire or particular segments of self-administered tests. Only target response motions in a test are captured and analyzed. Undesired motions that may interfere with assessment of users' cognitive and/or motor skills are reduced or excluded. When users' hands are anchored to the device, they will have limited ability to invalidate test results, for example by taking notes or hovering hands over regions of interest in spatial recall tasks. Task administration systems provide improvements in the accuracy and reliability of tests of neurological, cognitive, and motor skills, by ensuring that user inputs to such tests are valid inputs, etc.

20 Claims, 13 Drawing Sheets

MOTION RESTRICTION AND MEASUREMENT FOR SELF-ADMINISTERED COGNITIVE TESTS

CROSS-REFERENCE TO RELATED APPLICATION

This application claims priority under 35 U.S.C. §119(e) to U.S. Provisional Patent Application Ser. No. 62/063,000, "Method and system for ensuring valid data capture through the restriction of compensatory strategies during the self-administered collection of biometric and psychometric data via touchscreen computing devices," filed Oct. 13, 2014, which is incorporated herein by reference in its entirety.

BACKGROUND

1. Field of the Disclosure

The present invention relates to systems and methods for cognitive testing, and more specifically for a system and method for restricting user motions to collect data for self-administered cognitive testing.

2. Description of the Related Art

More than 90 million American suffer from a brain disorder that affects their daily functioning. These disorders can be psychological, emotional, motor, cognitive or social in nature. Neuropsychological and neurological testing to identify such disorders is generally performed by a mental health professional to measure a person's cognitive functions, such as memory function, language function, decision making, organization, attention span, reasoning, intellectual capacity, learning or any other brain related functions or disorders as well as motor, social, mood or emotional issues. Traditionally, neuropsychological tests are typically administered in-person using a pencil and paper or otherwise manual format. A candidate is placed in a quiet environment with a clinician and must answer a questionnaire on paper or perform some activity, which is observed and scored by the clinician. Since the traditional format for neuropsychological testing requires a highly skilled clinician, the costs of such testing are significant. In addition, in the United States there is approximately one neuropsychologist per 25,000 patients and one neurologist for every 35,000 patients, and a result, there is an insufficient number of skilled clinicians available to provide these tests to those who may suffer from some type of neurological deficit.

Accordingly, there is an interest in providing computer-mediated tests of neurological, cognitive and motor skills that can be self-administered by users. However, users, either intentionally or unintentionally, use compensatory strategies in an attempt to improve performance in the completion of such test, thereby resulting invalid or incorrect results.

SUMMARY

One embodiment of the computer-implemented method comprises configuring a touch-sensitive surface of a client device to present a computer-mediated, self-administered test to include a set of motion restriction regions and a user interface to receive a test input in response to the test. The set of motion restriction regions is configured on the touch-sensitive surface to restrict motion inputs to the touch-sensitive surface during the test. The computer-implemented method comprises starting the computer mediated test on the client device, and receiving the motion inputs on the touch-sensitive surface and the test input on the user interface during the test. The computer-implemented method further comprises determining whether one of the motion inputs on the touch-sensitive surface is a permitted input or a prohibited input in any of the motion restriction regions. Responsive to the motion input being a prohibited input, the computer-implemented method determines that the test input is invalid; and responsive to the motion input being a permitted input, the computer-implemented method determines that the test input is valid.

One embodiment of a non-transitory computer-readable storage medium storing executable computer program instructions for configuring a touch-sensitive surface of a client device to present a computer-mediated, self-administered test to include a set of motion restriction regions and a user interface to receive a test input in response to the test. The set of motion restriction regions is configured on the touch-sensitive surface to restrict motion inputs to the touch-sensitive surface during the test. The computer-readable storage medium store the executable computer program instructions for starting the computer mediated test on the client device, and receiving the motion inputs on the touch-sensitive surface and the test input on the user interface during the test. The computer-readable storage medium store the executable computer program instructions for determining whether one of the motion inputs on the touch-sensitive surface is a permitted input or a prohibited input in any of the motion restriction regions. Responsive to the motion input being a prohibited input, the test input is determined to be invalid; and responsive to the motion input being a permitted input, the test input is determined to be valid.

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

BRIEF DESCRIPTION OF THE DRAWINGS

The teachings of the present disclosure can be readily understood by considering the following detailed description in conjunction with the accompanying drawings.

Figure (FIG. 1 is a high-level block diagram illustrating an example environment for providing testing, according to one embodiment.

DETAILED DESCRIPTION

The Figures (FIG.) and the following description relate to various embodiments by way of illustration only. It should be noted that from the following discussion, alternative embodiments of the structures and methods disclosed herein will be readily recognized as viable alternatives that may be employed without departing from the principles discussed herein. Reference will now be made in detail to several embodiments, examples of which are illustrated in the accompanying figures. It is noted that wherever practicable similar or like reference numbers may be used in the figures and may indicate similar or like functionality.

In various embodiments, a client device is configured with a test administration application for conducting self-administered tests. The user interface of the test administration application includes motion restriction regions for restricting use of certain body parts (e.g., fingers, or hands) for purposes that are not intended by the test. For example, motion restriction regions are provided to anchor fingers from one or both hands to the touchscreen of the client device during self-administered tests in order to prevent taking notes during administration of verbal memory tests, to prevent hovering over areas of interest with unanchored hands during administration of spatial memory tests, and to prevent participation of an unintended hand during motor tests. Accordingly, only intended target responses in a test are captured and analyzed. Undesired motions that may interfere with assessment of users' cognitive and/or motor skills are reduced or excluded. Task administration systems provide improvements in the accuracy and reliability of tests of neurological, cognitive, and motor skills, by ensuring that user inputs to such tests are valid inputs, etc.

Figure 1:
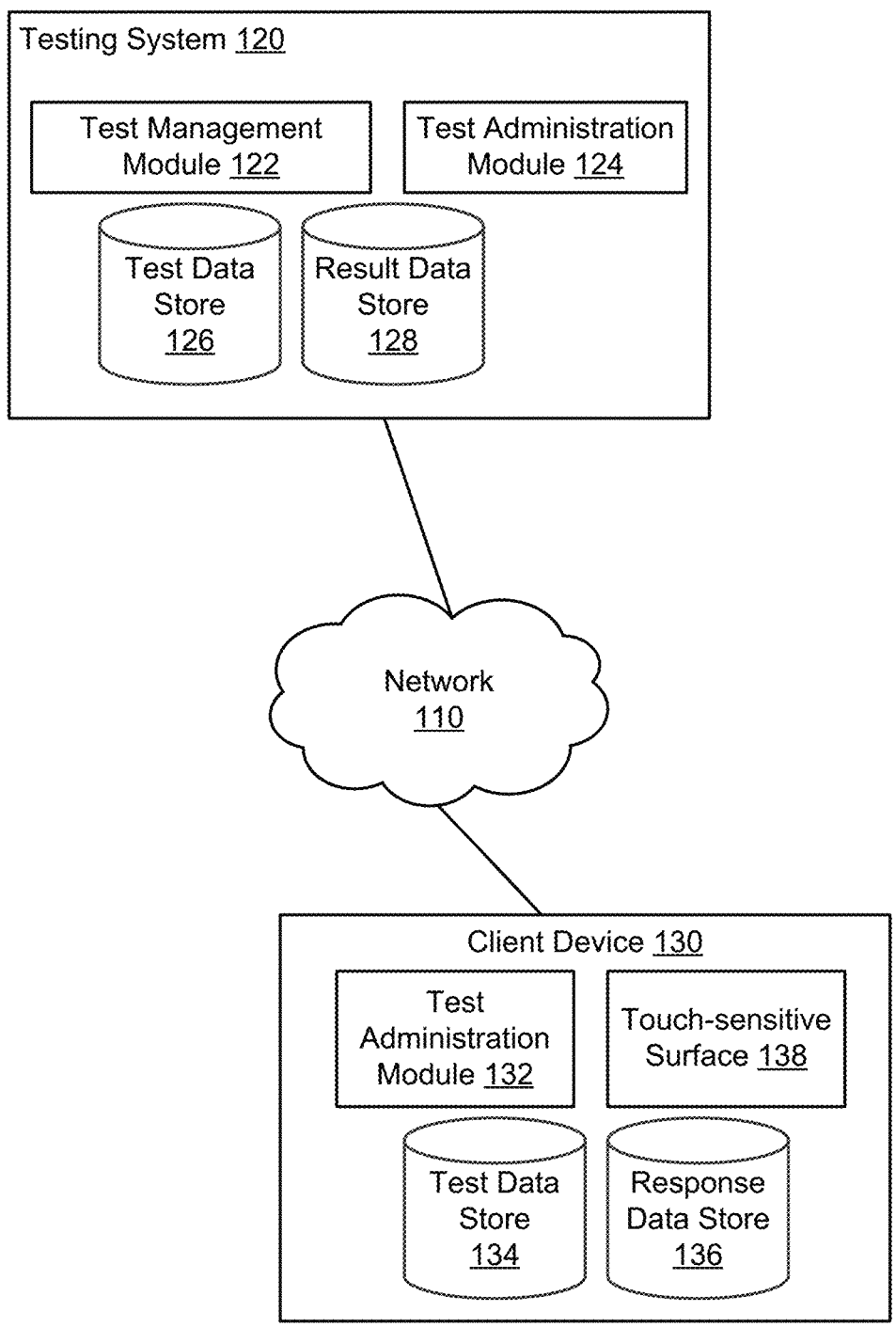

FIG. 1 is a high-level block diagram illustrating an environment 100 for providing testing, according to one embodiment. As shown, the environment 100 includes a network 110, a testing system 120, and a client device 130. The testing system 120 provides self-administered tests to users over a network 110 via client devices 130. While one testing system 120 and one client device 130 are shown in the example depicted in FIG. 1 for clarity, other embodiments may include different numbers of testing system and client devices. The testing system and its modules are not native components of the underlying computer(s) on which the testing system or client device executes, but rather extend the functionality beyond the generic functions of such computer(s) in the manner described herein.

The network 110 represents the communication pathway between the testing system 120 and the client device 130. In one embodiment, the network 110 uses standard wireless and wired communications technologies and protocols and can include the Internet and associated protocols. In another embodiment, the entities on the network 110 can use custom and/or dedicated data communications technologies.

The test management module 122 is configured for creating and managing tests that are designed to assess one or more cognitive capabilities (e.g., intelligence, learning ability, reasoning aptitude, cognitive development, memory, etc.) and/or motor skills (e.g., coordination of a certain group of muscle movement, synchronization of hands and fingers) of a user, and is one means for performing the functions as described. Tests can be tasks that require the users' to respond by completing the tasks using physical inputs to the client device, such as touches, taps, drags, using one or more fingers. A user's input response is measured and analyzed to assess the user's cognitive aptitude and/or motor skills in completing the task. For example, a test may involve manipulating graphical representations of objects such as blocks or icons, or memorization of sequences of presented stimuli to test cognitive skills, or a combination thereof. Some tasks may require speech inputs, for example where the user is required to verbally repeat a list of words, numbers, letters, or naming objects output to the user (either visually or auditorily from recorded prompts). In the case of verbal responses, the user interface of the client device is configured to receive the input, for example enabling a microphone of the client device, and initiating execution of a speech recognition algorithm (e.g., as disclosed in any of U.S. Pat. No. 5,956,671, 8,606,581, or 8,781,831 and incorporated by reference herein). The user speaks a response, and this verbal response is received via the user interface of the client device, recorded by the client device, and then processed using the speech recognition algorithm to identify the content of the response. The content is then compared with the predetermined responses to determine whether the user is correct. The test management module 122 allows an authorized user such as a clinician to create and configure a test such as configuring attributes associated with the test. A test may also include, a set of instructions prompts informing the user how to take the test, required responses, response analysis criteria, and the like. The test data store 126 stores tests and associated attributes.

The test administration module 124 manages, delivers, and conducts self-administered tests, and is one means for performing the functions as described. A self-administered test includes a series of tasks and is designed to assess one or more cognitive capabilities and/or motor skills of a user. The test administration module 124 selects a set of tests stored in the test data store 126 and/or orders the selected tests. The tests may be selected and/or ordered according to a predetermined plan or randomly. The test administration module 124 provides visual or audible instructions to the user on how to take a self-administered test, presents the tests on the client device via the presentation of graphical objects, images, symbols or the like, then receives the user inputs on the client devices in response to the test. Users' test results including the measurement and analysis of the users' performance are stored in the result data store 128.

A client device 130 is a computing device that includes a touch-sensitive surface 138, such as a touchscreen, or touchpad that enables a user to access the testing system 120 and/or to receive testing service provided by the testing system 120. A client device includes hardware and software modules to provide self-administered tests, to receive user input, and to connect to the network 110 (e.g., via Wi-Fi, Long-Term Evolution (LTE) or other wireless communication protocols). In one example provided throughout the description, the client device 130 is a tablet or smartphone including a touchscreen with operating systems such as ANDROID or APPLE IOS. The touchscreen can be used as both input and output interfaces. The term "module" refers to computer program logic utilized to provide the specified functionality upon execution by the client device 130. Other embodiments of a computing device or a client device 130 can have different and/or other modules than the ones described here, and that the functionalities can be distributed among the modules in a different manner.

The user may access the testing system 120 and/or to receive testing service provided by the testing system 120 in a variety of ways. In some embodiments, a user may download and install a client application of the testing system 120 on the client device 130. Accordingly, as illustrated, in one embodiment, the client device 130 may include a test administration module 132 for delivering and conducting self-administered tests to the user, a test data store 134, and a result data store 136. The test data store 134 may store all or a subset of the tests stored in the test data store 126. The testing system 120 may periodically provide tests to a client device 130. The result data store 136 may store a users' response data such as users' motion data, analysis of users' motion data, users' performance in tests, and the like. The test administration module 132 provides instructions to the user on how to take a self-administered test, monitors, measures, and analyzes the user's performance, and/or returns the user's test result to the user. In some embodiments, a user may access the testing system 120 by logging into the user's account of the testing system 120 using the user's credentials (e.g., using a username/password combination) via the client device 130. The user may take a self-administered test on the testing system 120. A more detailed description of the client device 130 is provided in connection with FIGS. 2 through 11.

Client Device

Figure 2A:
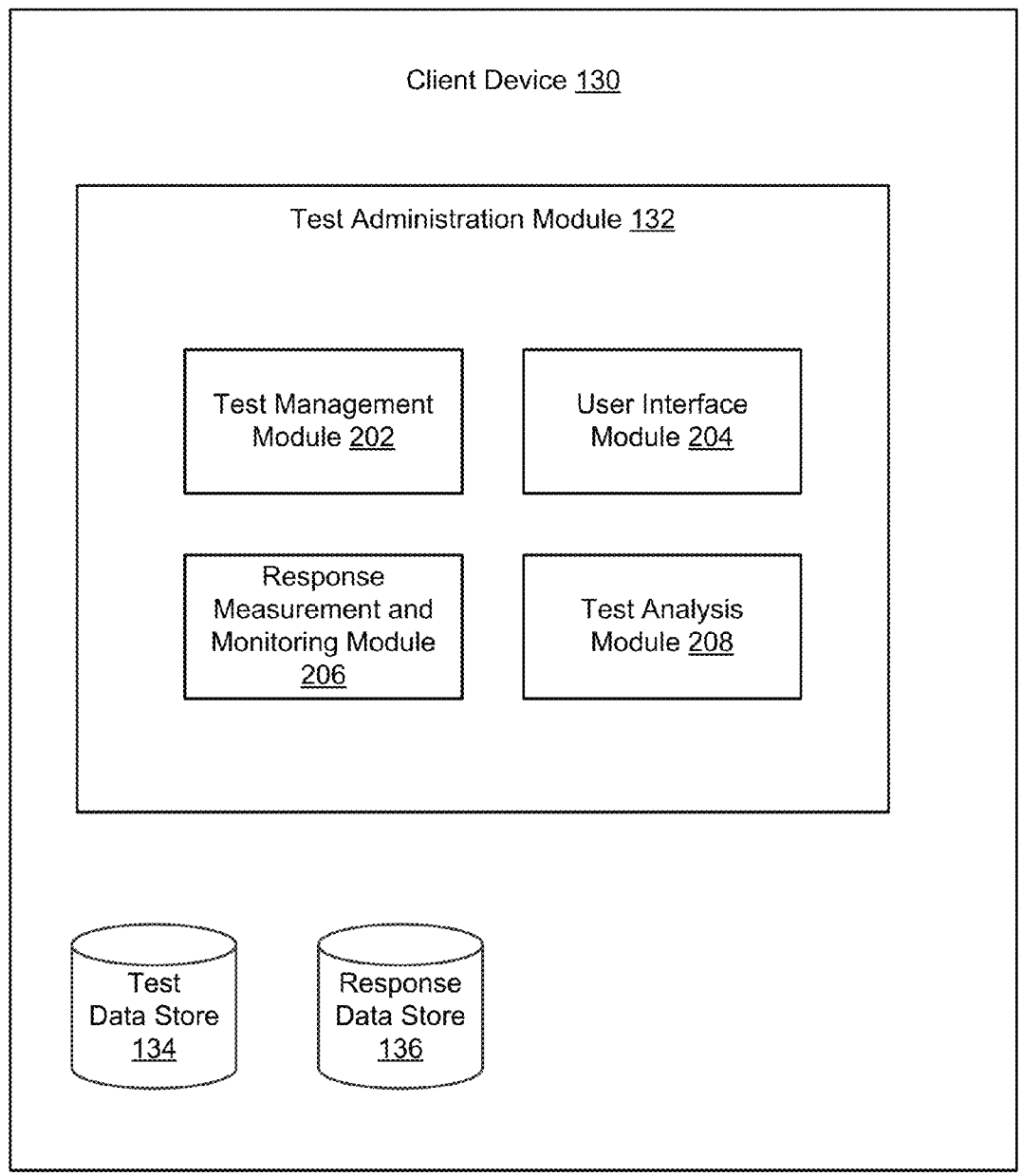
FIG. 2A is a block diagram of an example client device, according to one embodiment.

FIG. 2A is a block diagram of a client device 130, according to one embodiment. The client device 130 comprises a touch-sensitive surface 138, such as a touchscreen, touchpad, or the like, a test administration module 132, a test data store, and a response data store 136. As described in connection with FIG. 1, the test administration module 124 manages, delivers, and conducts self-administered tests. The test administration module 124 allows a user to take a self-administered test. The user provides inputs to the test via the touch-sensitive surface.

The test data store 134 stores various tests that can be taken by a user. Each test stored in the test data store 134 is associated with a set of attributes such as an objective (e.g., to evaluate an cognitive skill, to evaluate an evaluated motor skill, to diagnose a disorder), an instruction (e.g., text, media items such as images, video clips, sound tracks, etc.) to users, a required response (e.g., a particular type of motion, a location of the motion, a timing of the motion, etc.), prohibited motion (e.g., one or more motion restriction regions), measuring of the user's motion (e.g., isolation of motion, etc.), evaluation criteria, etc. The response data store 136 stores the measurement of a user's response to tests.

The test administration module 132 comprises a test management module 202, a user interface module 204, a response measurement and monitoring module 206, and an optional test analysis module 208. The test management module 202 configures tests for presentation to a user and then administers the tests to the user, and is one means for performing the described functions. The test management module 202 may select a set of tests based on the user's test request. The test management module 202 configures the presentation of a test to ensure the test accurately and reliably assesses the user's cognitive and/or motor skills, and is one means for performing the described functions. Users may attempt to use compensatory strategies to improve their performance, either intentionally or unintentionally. For example, when a user takes a memory test comprising the presentation of list of words on the display of the client device, the user may intentionally attempt to write down the list of words on notepad rather than memorizing it to improve his performance. Or, a user may provide additional inputs to the device using additional fingers. The test management module 202 configures a test such that users are prevented from using these and other compensatory strategies may result in invalid responses that do not reflect actual the actual cognitive or motor skills being tests, and thus the module 202 ensures that a user's response to the test is valid and reliable.

The test management module 202 configures a user interface associated with a test to include one or more motion restriction regions on the touch-sensitive surface 138 for conducting the test. A motion restriction region are locations on the touch-sensitive surface 138, such as a touchscreen of the client device, on which the user must perform a predetermined action (e.g., maintain constant contact with one or more fingers of one or both hands) during the test. The predetermined action may constrain the movement of a user's body part (e.g., finger, hand, wrist, elbow, shoulder, etc.) While the user is performing the predetermined action in motion restriction region and the particular body part is being constrained, the user provides inputs as responses to the test non-constrained body parts (e.g., using other fingers of one or both hands that are free) or voice. The constraint on the motion of particular body part(s) ensures that the user has not employed any compensatory strategies, and thus the actual input on the touch-sensitive surface 138 is valid. For example, ensuring that fingers of both hands are in constant contact with the motion restriction region during the test prevents the user from using one hand to write notes or information useful for performing the test, such as writing down a list of words presented during the test to be remembered by the user. For purposes of convenience, in the following descriptions, the touch-sensitive surface is a touchscreen of the client device.

As one example, a motion restriction region is a predefined anchoring region (e.g., a circle with a center and a radius) displayed on the touchscreen of the client device. The anchoring region requires one or more of the user's fingers to be anchored to the circle on the touchscreen of the client device during the administration of the test. That is, once the user's finger contacts an area of the touchscreen in the circle, the user's finger is registered to that particular area and required to make a constant contact with the particular area of the touchscreen during the test. As such, the user's finger is prevented from moving away from the particular area of the touchscreen. The user's other body parts such as other fingers, shoulders, wrists, or elbows may also be prevented from moving by this motion restriction region even though they are not making contact with the client device as their movement will cause the user's finger to move off of the anchoring region during the test. If the user's finger loses contact with the anchoring region during the test, the test can be started over, or inputs received from the user while the contact with the anchoring regions is broken are indicated as being invalid.

The test management module 202 may configure one or more motion restriction regions included in the user interface associated with the test. The test management module 202 configures the motion restriction regions (e.g., a location, a time period, a size, permitted motions, prohibited motions, instructions, a distance from another motion restriction region, etc.) as defined in the test. For example, for a test that requires fine control of particular muscles, the test management module 202 configures the motion restriction regions as defined in the test to arrange the user's fingers into predetermined positions such that the user's control of the particular muscles can be assessed by restricting the motion of fingers that are not being tested.

As some tests do not require inputs from both hands or ten fingers, the test management module 202 configures one or more motion restriction regions to prevent interference or performance enhancement from the use of the free hand or finger. For example, when a test requires a user to use her left hand, the test management module 202 may configure one or more motion restriction regions to anchor the user's right hand to the client device, thereby preventing the user from providing inputs with the right hand. For example, when a test requires a user to use the index finger of her non-dominant hand to perform pivoted finger tapping, the test management module 202 can configure six motion restriction regions on the touchscreen of the device: four to anchor the user's thumb, index, middle, and pinky fingers of the non-dominant hand, and two to anchor the user's thumb and middle finger of the dominant hand, thereby effectively ensuring that only the non-dominant index finger can provide inputs during the test. The test management module 202 configures the four motion restriction regions separated by a distance such that the four fingers are anchored in a substantially natural way, leaving a remaining finger on the non-dominant hand free to provide the required tapping inputs. The test management module 202 configures the two remaining motion restriction regions separated from the other four motion restriction regions such that the user cannot use the other fingers of her dominant hand to aid tapping. This is just one example of how motion restriction regions may be used; other examples are described below.

For tests that require users' motion response, the test management module 202 configures a user interface associated with a test that includes one or more testing regions on the touchscreen. A testing region is a region on the touchscreen to receive a touch input as a target response from the user. The test management module 202 configures the testing region(s) (e.g., a location, a time period, a size, permitted motions, prohibited motions, instructions, a distance from another motion restriction region, etc.) as defined in the test. For example in a finger tapping test of the non-dominant hand, the user is required to tap the index finger of her left hand within the testing region. Tapping the index finger outside the testing region is an invalid response. The test management module 202 thus displays a testing region according on the display in which to receive the finger taps, and then one or more anchoring regions to receive touches from fingers from one or both hands. For tests that require users' voice input, the test management module 202 configures a user interface (e.g., a voice-user interface) to recognize the user's speech input.

There are various different arrangements of motions restriction regions that may be used. In one embodiment, the test management module 202 configures the user interface to include motion restriction regions for anchoring a user's thumb and any three fingers of index, middle, ring, and pinky fingers of the right or left hand. The user interface is configured to include a testing region for the other finger that is not restricted (e.g., index, middle, ring, or pinky). The motion restriction regions and the testing region each are a circle. The centers and radius of the circles as well as the distance between the circles are configured such that the user's hand and fingers are positioned substantially naturally and comfortably when five fingers being positioned in the respective motion restriction region or testing region.

Other embodiments provide the following combinations of motion restriction regions:

1) third finger and thumb anchored on tested hand and three anchored digits on opposing hand;
2) third finger and thumb anchored on tested hand and two anchored digits on opposing hand;
3) third finger and thumb anchored on tested hand and three anchored digits on opposing hand;
4) three fingers anchored with thumb unanchored on tested hand and two anchored digits on opposing hand;
5) three fingers anchored with thumb unanchored on tested hand and three anchored digits on opposing hand;
6) third finger anchored on tested hand and two anchored digits on opposing hand; or
7) third finger anchored on tested hand and three anchored digits on opposing hand.

The test management module 202 configures the user interface for conducting the test to ensure that instructions associated with a test, motion restriction regions, and/or testing regions are accurately presented to the user. The instructions associated with a test, a motion restriction region, or testing region provides information to a user to enable the user to understand and respond to the test and the test in in a controlled manner such that the user's response meets the motion requirement. For instance, display attributes such as the font, volume, color, and the like of user interface elements are configured to ensure that instructions associated with a test, or a motion restriction region, are displayed to a user. Instructions can be visual or auditory.

The user interface module 204 presents the user interface as configured by the test management module 202 for conducting a test, and is one means for performing the described functions. The user interface module 204 presents various user interface elements, motion restriction regions, testing regions, or instructions associated with the test, motion restriction region, or testing region visually or auditorily. For example, the user interface module 204 renders and presents visual objects such as texts or graphics, auditory signals such as speech or music. For example, graphics include text, web pages, icons including user-interface objects including soft keys, digital images, videos, animations, and the like. The user interface module 204 may include computer executable instructions to enable users to respond to a test or comply with motion restriction requirement. For example, the user may identify and select regions, portions, locations, or user interface elements presented on the display screen.

In some embodiments, the test management module 202 may configure the user interface dynamically, for example, based on the user's response. The user's response may be detected by the response measurement and monitoring module 206. For instance, upon detecting that a user is partially following instructions, the test management module 202 configures the user interface to include the instructions that need to be followed by the user. Continuing with the example of the test requiring the user to use her non-dominant hand to perform pivoted finger tapping for example, the user has anchored her index, middle, and pinky fingers of but has not anchored the thumb of the non-dominant hand. The test management module 202 may configure the user interface to highlight the motion restriction region for anchoring the user's thumb of the non-dominant hand.

The response measurement and monitoring module 206 detects users' inputs such as motion inputs on the touch-sensitive surface, including inputs in the motion restriction regions and testing regions as well as speech input, and is one means for performing the described functions. For example, the response measurement and monitoring module 206 detects a motion input by a user on touchscreen of the client device 130 or a speech input by a user on voice-user interface of the client device 130. The response measurement and monitoring module 206 generates response data including motion data and/or voice data based on a user's motion or speech input. The touch-sensitive surface 138 of the client device 130 supports multi-touch motions. Different motions have different touch patterns. A touch pattern is characterized by one or more touch points and their associated movements, from which the spatial or geometrical relationships between the touch points can be determined. The response measurement and monitoring module 206 may use the touch event data to generate motion data to measure a user's motion when a motion is detected and store the motion data in the response data store 136. In some embodiments, motion data includes motion events as well as the time, locations, and classifications (e.g., restricted, test, free) of the motion events. The response measurement and monitoring module 206 compares the location of a motion event to a location of a motion restriction region or of a testing region to determine the classification of a motion event. A motion event is restricted when its location is within a motion restriction region, test when its location is within a testing region, or free when its location is neither within a motion restriction region nor within a testing region.

In some embodiments, the response measurement and monitoring module 206 receives from the underlying operating system motion events including a finger-down event, a finger-up event, and a finger-move event. A finger-down event indicates an initial touch of a position (e.g., a horizontal position and a vertical position) on the touchscreen of the client device 130. A finger-up event indicates the finger is no longer touching the touch screen at substantially the same position as the finger-down event. A finger-move event indicates the finger moves away from the position associated with the finger-down event. A motion event is associated with a time stamp indicating the time of the event.

The response measurement and monitoring module 206 monitors the user's response to validate whether a user responds in a controlled manner, and is one means for performing the described functions. A user's response is monitored and validated to ensure that user is following the instructions and responding as required by the test. For example, the response measurement and monitoring module 206 monitors the user's motion in a motion restriction region to determine whether the user is constraining his or her body part movement to those motions permitted by the motion restriction region or the user's motion in the motion restriction region is not prohibited by the motion restriction region. As one example, the response measurement and monitoring module 206 determines from the motion data whether a user anchors the user's hands as required when the user is repeating the list of words presented during a test, by detecting whether any of the user's fingers have lifted off of the motion restriction regions or moved out of these regions, in which case the test may be terminated (or restarted) or the user's response to the test is considered as invalid and discarded.

In some embodiments, the response measurement and monitoring module 206 monitors the user's response by evaluating and analyzing the motion data generated. For example, restricted motion events are compared to identify a user's movement in the motion restriction region and the identified movement is compared to the movements permitted or prohibited in the motion restriction region. When the response measurement and monitoring module 206 detects that the user's movement in the motion restriction region is not permitted or prohibited, the user's response is determined as invalid. Generally, during a test, a finger-up event in a motion restriction region, or movement out of the boundaries of a motion restriction region is prohibited.

When the response measurement and monitoring module 206 determines that the user is not responding as permitted by the test, the test administration module 132 may conduct the test in a variety of ways. In some embodiments, the test administration module 132 may terminate or restart the test. Alternatively, the test management module 202 alerts the user that he and she has violated the test requirement and continues administering the test. The test management module 202 may determine that the response data point generated at the time of the prohibited motion event fails to comply with the test requirement is invalid and discard the response data point. In some embodiments, the response measurement and monitoring module 206 may associate the motion data with a record that the user has failed to constrain his or her movement without terminating the test. The motion data with the record can be analyzed along with other generated motion data.

The test analysis module 208 evaluates a user's performance in the test, and is one means for performing the described functions. The test analysis module 208 may analyze the response data including motion data and/or voice data collected by the response measurement and monitoring module 206 during the test to evaluate the user's performance. In some embodiments, the test analysis module 208 may analyze a user's performance in real time simultaneously when the response measurement and monitoring module 206 measuring a user's response. In some embodiments, the test analysis module 208 may analyze a user's performance until the test is complete. The test analysis module 208 may analyze a user's response to each test included in the test determines the user's performance in the test as an aggregation of all the tests of the test. The user's response to each test included in the test may be evaluated by using the required response and/or evaluation criteria associated with the test. The test analysis module may store a user's performance in tests in the response data store 136.

Method of Conducting a Self-administered Test

Figure 2B:
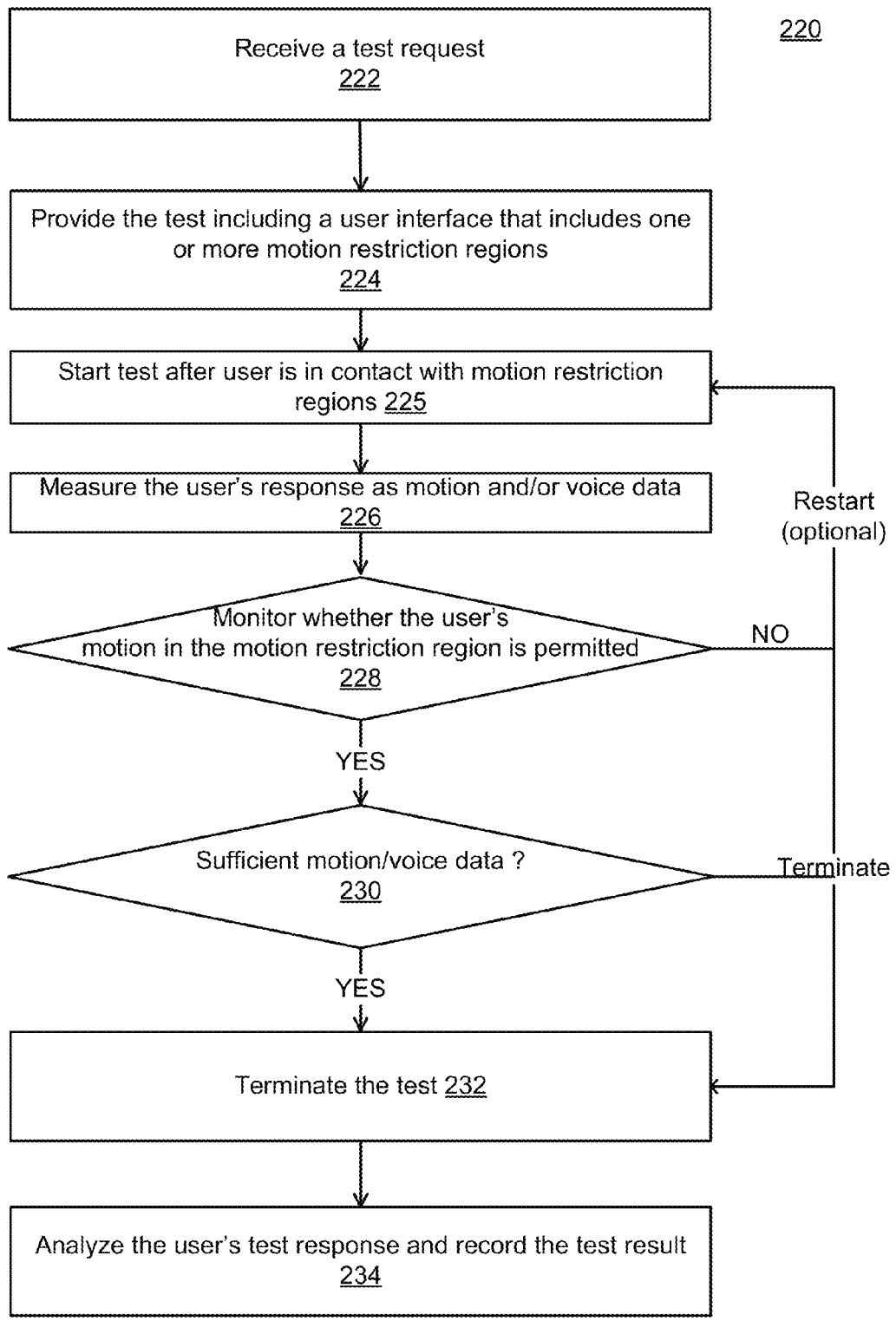
FIG. 2B is a flow diagram of an example method of conducting self-administered tests, according to one embodiment.

FIG. 2B is a flow diagram illustrating an example method 220 of conducting a self-administered test, according to one embodiment. The test administration module 132 receives 222 a test request from a user. A self-administered test includes a series of tasks to assess one or more cognitive capabilities and/or motor skills of a user. The test administration module 132 selects tests as requested by the user. The test administration module 132 retrieves the test from the test store.

The test administration module 132 presents 224 the touch-sensitive surface 138 of the client device to include at least one motion restriction region. The test may define a predetermined number of motion restriction regions as well as the associated attributes, according to which the test administration module 132 configures the test. A motion restriction region and associated instructions constrain a user's body part (e.g., finger, hand, wrist, elbow, shoulder, etc.) movement. Where the touch-sensitive surface 138 is the touchscreen of the client device, the motion restriction regions and testing regions are graphically indicated. The test administration module 132 further configures one or more user interfaces for conducting the test to present instructions associated with a test, motion restriction regions, and/or testing regions are accurately presented to the user. The test administration module 132 may configure a voice-user interface to recognize a user's speech input.

The test administration module 132 waits until the user's fingers are in contact with the variously configured motion restriction regions, and then starts 225 the test. The user may be required to be in contact with the motion restriction regions for a minimum amount of time, for example three seconds, or for the duration of the stimuli display or the testing period. Once the test is started, the test administration module then receives 226 the inputs as motion data and/or voice data to measure the user's response. In some embodiments, motion data includes motion events as well as time, locations (e.g., a position (x,y) on the touchscreen), and classifications (e.g., restricted, test, free) of the motion events. For example, the response measurement and monitoring module 206 generates motion events including a finger-down event, a finger-up event, and a finger-move event. A finger-down event indicates an initial touch of a position on the touchscreen of the client device 130. A finger-up event indicates the finger is no longer touching the touch screen at substantially the same position as the finger-down event. A finger-move event indicates the finger moves away from the position associated with the finger-down event. The response measurement and monitoring module 206 compares the location of a motion event to a location of a motion restriction region or of a testing region to determine the classification of a motion event. A motion event is restricted when its location is within a motion restriction region, test when its location is within a testing region, or free when its location is neither within a motion restriction region nor within a testing region.

The test administration module 132 analyzes the motion events to identify a user's motion in the motion restriction region based on the location of the motion event. In various embodiments, the test administration module 132 further determines the timing (e.g., the duration), type of movement (e.g., lift, constant contact, move, etc.), magnitude (e.g., amount of movement) of a motion. For instance, the test administration module 132 compares restricted consecutive motion events to determine the movement in the motion restriction region. As one example, a finger-down event followed by a finger-up event in the motion restriction region indicates that the user's finger is lifted. As another example, a finger down-event followed by a finger-move event in the motion restriction region indicates that the user's finger has moved. The magnitude of the movement is determined as the difference between the locations associated with the two events. The speed of the movement is determined as the difference between the locations associated with the two events divided by the difference between the time stamps associated with the two events. The direction of the movement can be determined by comparing the locations associated with the two events. As a further example, a finger-move event followed by another finger-move event in the motion restriction region indicates that the user's finger has moved. The magnitude, speed, and direction of the movement can be determined similarly as the example of a finger down-event followed by a finger-move event. In some embodiments, the test administration module 132 registers the first finger-down event in a motion restriction region and analyzes subsequent events in the motion restriction region to determine the user's motion in the motion restriction region in reference to the first finger-down event.

The test administration module 132 monitors 228 whether any motion events in the motion restriction region(s) are permitted or prohibited. The test administration module 132 thereby can determine whether a user is following the instructions and responding as required by the test. The test administration module 132 may compare the determined user's motion in the motion restriction region to a predetermined permitted motion or a predetermined prohibited motion to determine whether the contemporaneous user input in the testing region is valid. For example, the test administration module 132 may compare the timing (e.g., the duration), type of movement (e.g., lift, constant contact, move, etc.), magnitude (e.g., amount of movement) and the like of a determined motion to those of a predetermined permitted/prohibited motion determine whether a motion is a permitted/prohibited motion. When a motion in a motion restriction region is permitted, the user's input to the test (e.g., motion input in the testing region or speech input) is valid; and when a motion in a motion restriction region is prohibited, the user's corresponding input to the test is invalid. For example, the test administration module 132 determines a finger-lifting movement in an anchoring region (i.e., finger-down event followed by a finger-up event) is prohibited motion and therefore an input received in the testing region is invalid. The test administration module 132 may determine a finger-move movement in an anchoring region (e.g., a finger-down event followed by a finger-move event), of which the magnitude is less than a threshold magnitude permitted in the anchoring region and therefore the user's input in the testing region is valid. Conversely, a finger-move movement with a magnitude greater than a threshold magnitude permitted in the anchoring region is prohibited motion and therefore the user's input in the testing region is invalid. The user input may be contemporaneous (e.g., in testing such as finger-tapping, line matching, motion tracking, or the like) or may be subsequent (e.g., in tests requiring the memorization of stimuli and their subsequent input).

Depending on the test configuration, the test administration module 132 terminates 232 the test subsequent to determining the user's motion in the motion restriction region is invalid. Alternatively, the test administration module 132 restarts 225 the test; in this case, the test administration module 132 maintains a count of the number of attempts by the user to take the test, and may suspend further testing if a maximum number (e.g., three attempts) is reached.

In some embodiments, the test administration module 132 determines 230 whether a predetermined amount of motion and/or voice data has been collected. A test requires sufficient motion data to be collected to analyze the user's performance. In other embodiments, the test administration module 132 measures the user's response until the test is complete. In some embodiments, where the test administration module 132 restarts the test, it may determine 230 if a sufficient amount of motion data has been collected during the one or more attempts. If so, the test administration module 132 terminates 232 the test subsequent to determining the sufficient amount of motion data has been collected. The test administration module 132 optionally analyzes 234 the user's test response and records the test result in the response data store 136. The test administration module 132 may analyze the collected motion data as defined in the test to evaluate the user's performance in the test. The test administration module 132 may analyze a user's performance simultaneously when the user is taking a test or after the user completes a test. In some embodiments, the test administration module 132 may provide a user's response data or a portion thereof to a server (e.g., the testing system 120 illustrated in FIG. 1) for further analysis and/or diagnosis.

Figure 2C:
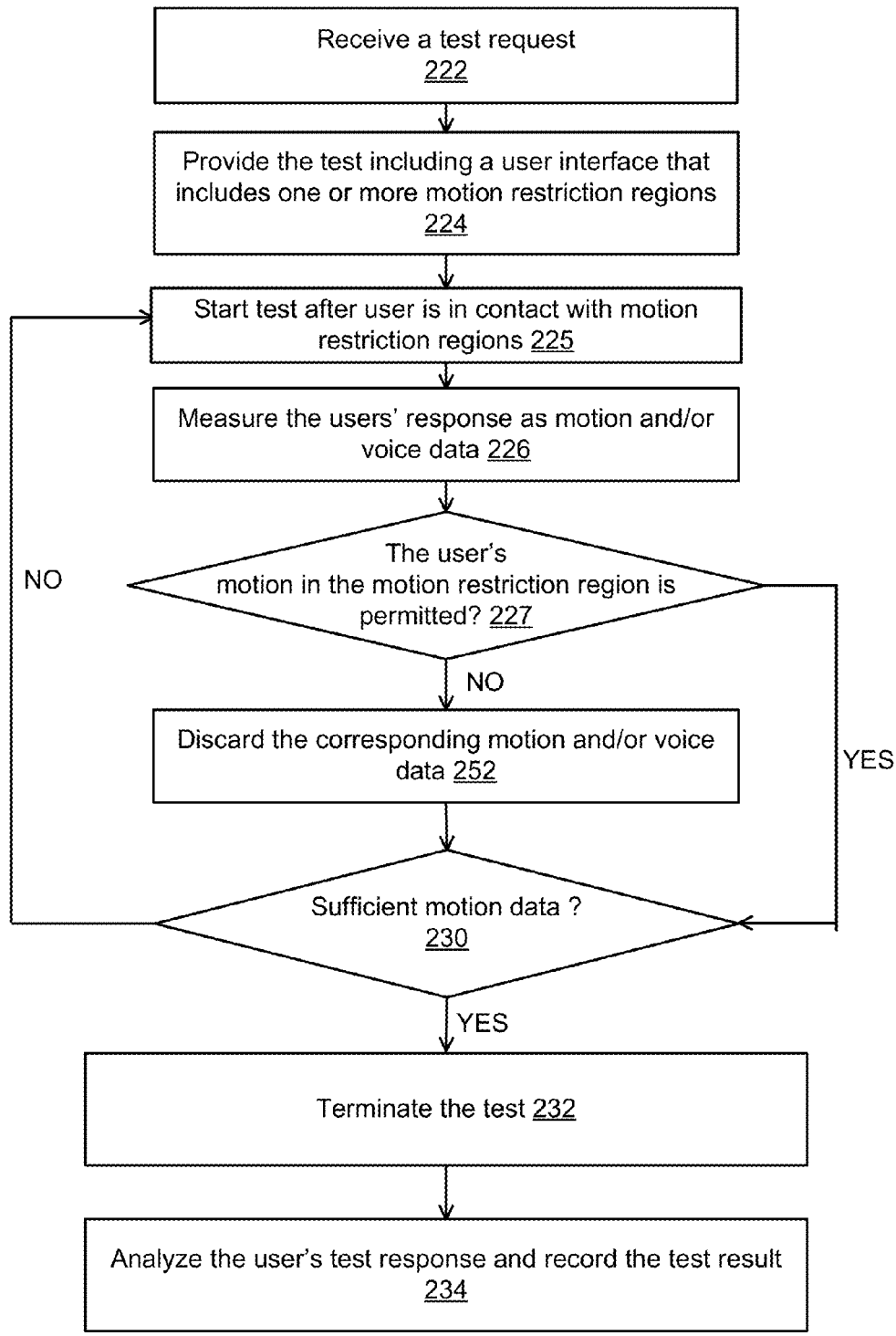
FIG. 2C is a flow diagram illustrating an example method of conducting a self-administered test, according to one embodiment.

FIG. 2C is a flow diagram illustrating another embodiment of a method 250 of conducting a self-administered test, according to one embodiment. The method 250 illustrated in FIG. 2C is similar to the method 220 illustrated in FIG. 2B and accordingly the same steps and related descriptions are omitted herein. Subsequent to determining the user's motion in the motion restriction region is prohibited, rather than terminating the test as illustrated in FIG. 2B, the test administration module 132 continues to discard 252 the input data received in the testing region of a user interface or over the voice-user interface, or otherwise annotates the input data as being invalid. For example, during a test that requires a user to tap a specific finger in a specific testing region, various fingers from both hands are to be anchored to prevent the user inputting additional taps with other fingers. When the test administration module 132 detects that one or more of the other fingers have lifted off of the motion restriction regions, the test administration module 132 discards the user's corresponding input in the testing region because it is invalid. This is because the received input in the testing region that may not reflect the user's actual performance for the specified finger. In some embodiments as illustrated, the test administration module 132 continues conducting the test until a predetermined amount of motion data sufficient for analyzing the user's response is collected. In other embodiments, the test administration module 132 continues conducting the test until the test completes.

Computer Diagram

Figure 3:
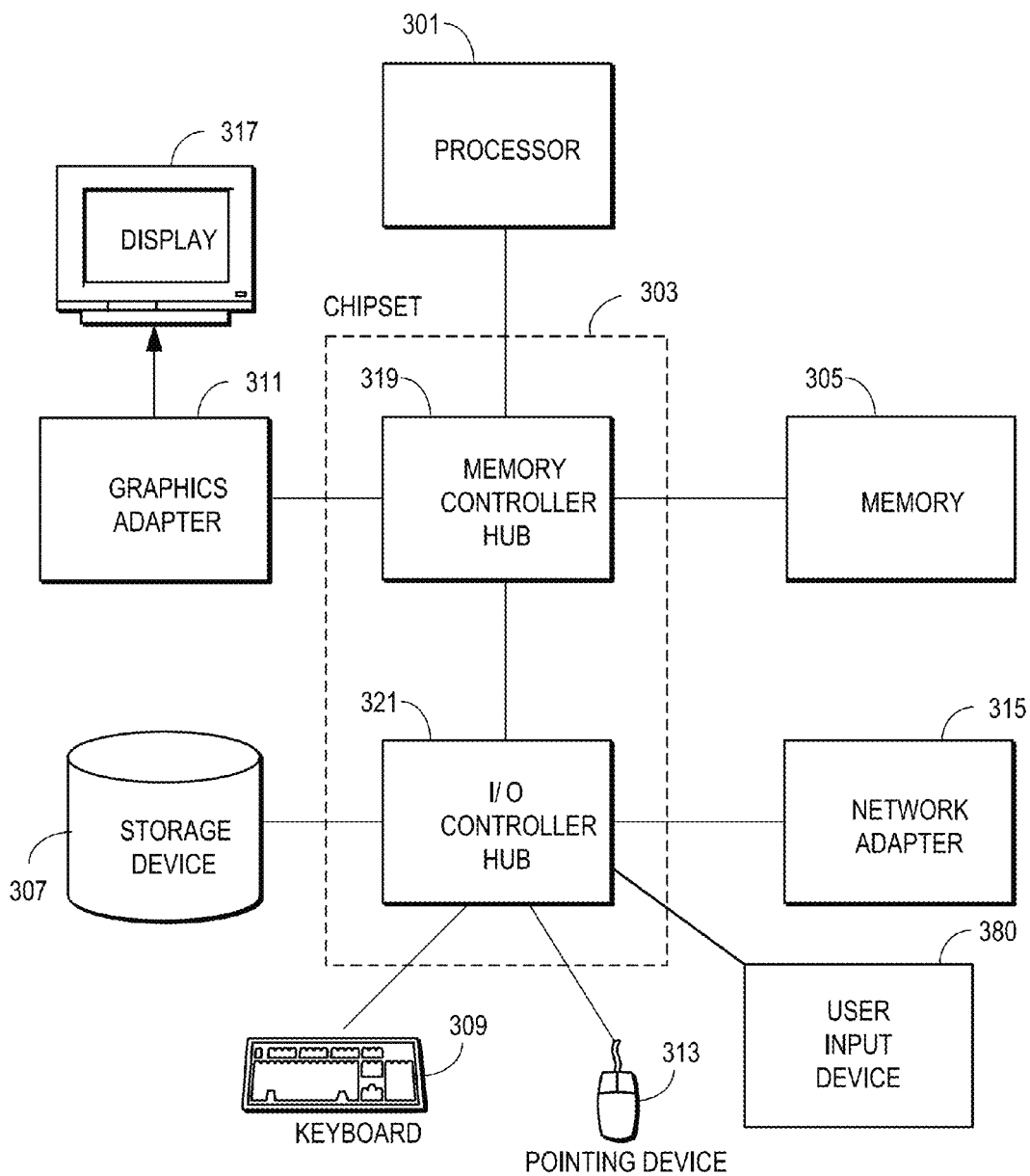
FIG. 3 is a high-level block diagram illustrating a typical computer for acting as a computing device, according to one embodiment.

FIG. 3 is a high-level block diagram of a computer 300 for example, for acting as a computing device according to some embodiments. Illustrated are at least one processor 301 coupled to a chipset 303. Also coupled to the chipset 303 are memory 305, a storage device 307, a keyboard 309, a graphics adapter 311, a pointing device 313, and a network adapter 315, and touch-sensitive surface 380. A display 317 is coupled to the graphics adapter 311. In one embodiment, the functionality of the chipset 303 is provided by a memory controller hub 319 and an I/O controller hub 321. In another embodiment, memory 305 is coupled directly to the processor 301 instead of the chipset 303.

The storage device 307 is any non-transitory computer-readable storage medium, such as a hard drive, compact disk read-only memory (CD-ROM), DVD, or a solid-state memory device. Memory 305 holds instructions and data used by the processor 301. The pointing device 313 may be a mouse, track ball, touch panel, or other type of pointing device, and is used in combination with the keyboard 309 to input data into the computer 300. The touch-sensitive surface 380 is configured to receive touch inputs (including multi-touch inputs). In some embodiments the touch-sensitive surface 380 may be integrated into the display 317, for example in a touchscreen. The graphics adapter 311 displays images and other information on the display 317. The network adapter 315 couples the computer 300 to a local or wide area network (e.g., the network 110 illustrated in FIG. 1).

As is known in the art, a computer 300 can have different and/or other components than those shown in FIG. 2A. In addition, the computer 300 can lack certain illustrated components. As is known in the art, the computer 300 is adapted to execute computer program modules for providing functionality previously described herein. In one embodiment, program modules are stored on the storage device 307, loaded into memory 305, and executed by the processor 301.

Example User Interfaces

Figure 4A:
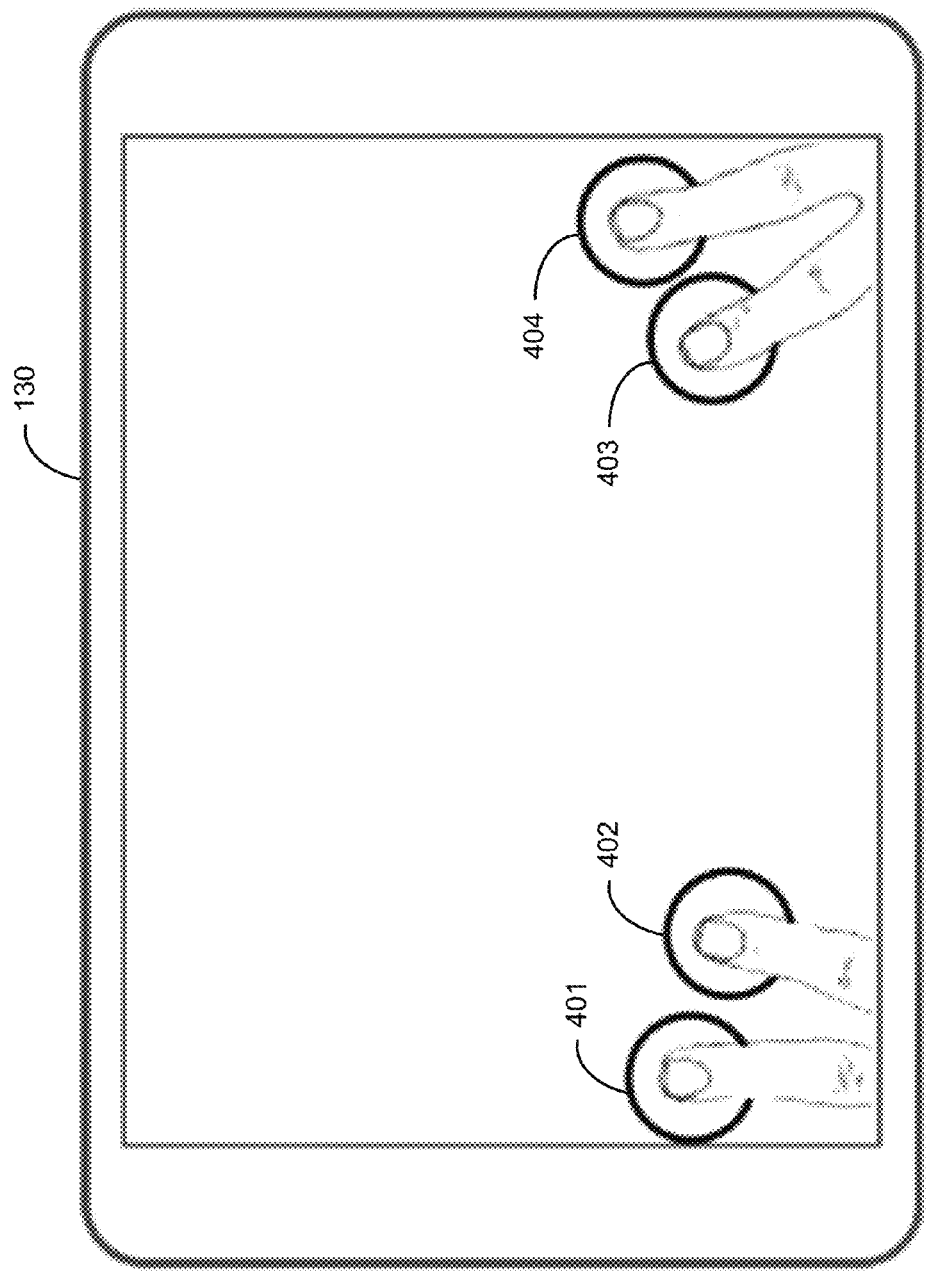
FIG. 4A illustrates an example user interface for conducting self-administered tests, according to one embodiment.
Figure 4B:
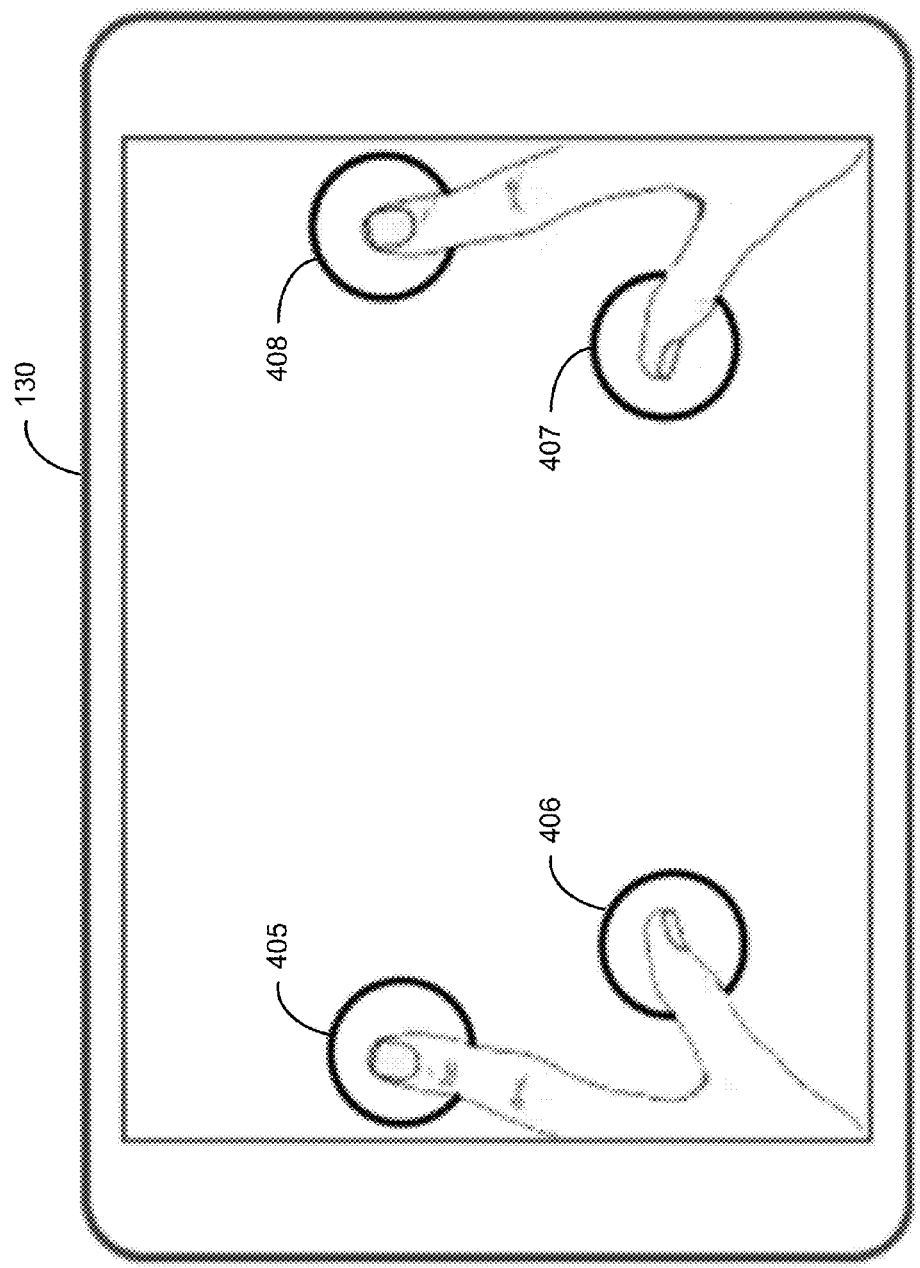
FIG. 4B illustrates an example user interface for conducting self-administered tests, according to one embodiment.
Figure 4C:
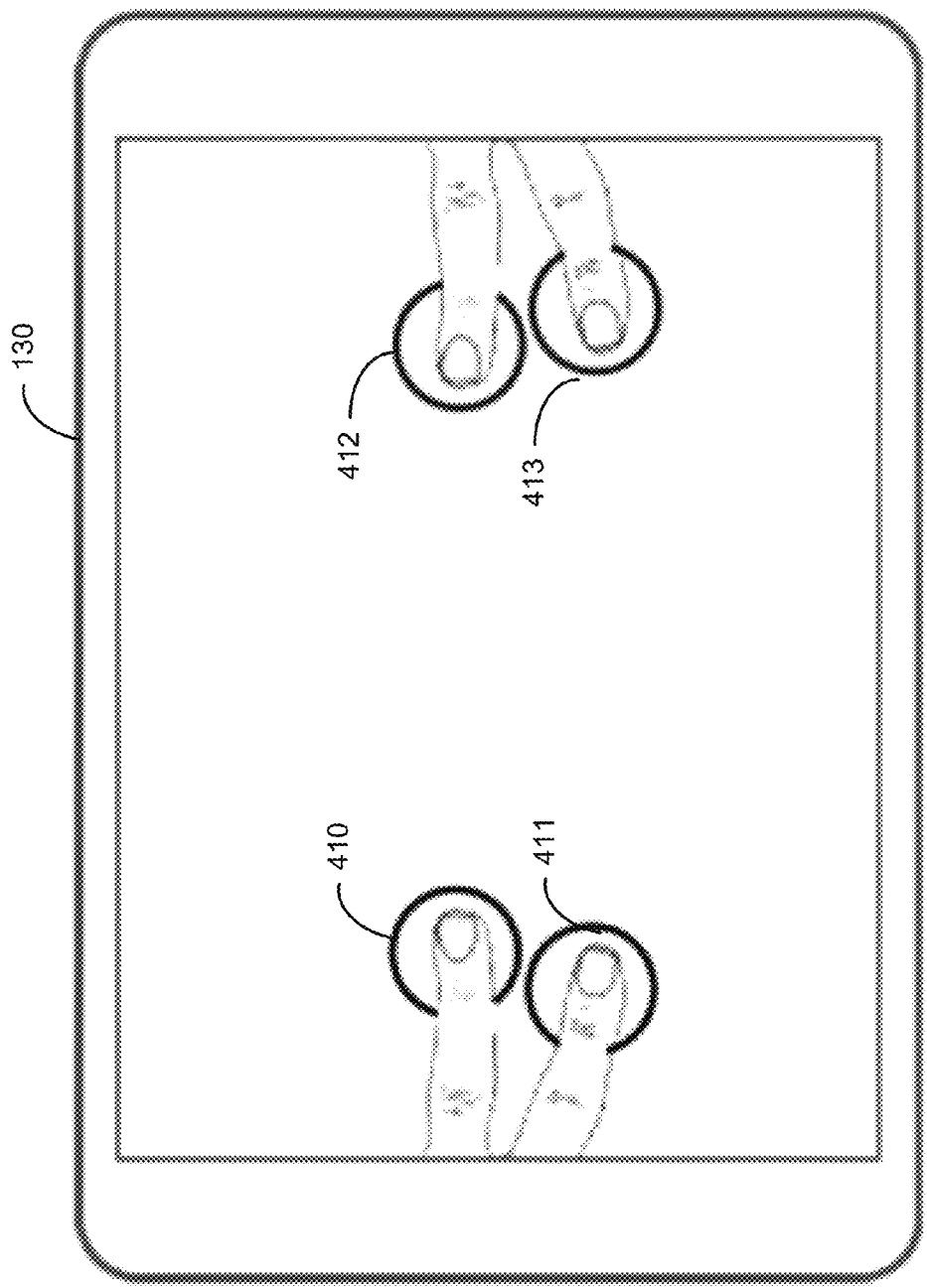
FIG. 4C illustrates an example user interface for conducting self-administered tests, according to one embodiment.

FIGS. 4A through 4C each illustrate an example user interface of self-administered tests, according to one embodiment. The illustrated example user interface for a test is presented on the client device 130 in FIG. 4A and includes motion restriction regions 401 through 404. The motion restriction regions 401 and 402 are for anchoring the middle and index fingers of a user's left hand, and motion restriction regions 403 and 404 are for anchoring the index and middle fingers of the user's right hand. As illustrated, the motion restriction regions 401 and 404 for anchoring the left and right middle fingers are positioned higher on the display than the motion restriction regions 402 and 403 for anchoring the left and right index fingers, respectively, thus resulting in positioning of the hands in a natural orientation. In addition, the centers of the motion restriction regions 401 and 402 as well as the centers of the motion restriction regions 403 and 404 are separated by an average distance between the tips of an adult's middle and index fingers when the hand is in a relaxed position. Furthermore, the motion restriction regions 401 and 402 and the motion restriction regions 403 and 404 are positioned such that the user's left and right hands are anchored to the lower left and right corners of the client device 130 and the other fingers (i.e., ring and pinky) are substantially prevented from touching the touchscreen of the client device 130.

The illustrated example user interface presented on the client device 130 in FIG. 4B includes motion restriction regions 405 through 408. The motion restriction regions 405 through 408 anchor a user's left and right thumbs as well as index fingers. As illustrated, the motion restriction regions 405 and 408 for anchoring the left and right index fingers are positioned higher than the motion restriction regions 406 and 407 for anchoring the left and right thumbs, respectively. In addition, the centers of the motion restriction regions 405 and 408 as well as the centers of the motion restriction regions 406 and 407 are separated by an average distance between the tips of an adult's thumbs and index fingers. Furthermore, the motion restriction regions 405 and 406 and the motion restriction regions 407 and 408 are positioned such that the user's left and right hands are anchored to the left and right edges of the client device 130 and the other fingers are prevented from touching the touchscreen of the client device 130.

The illustrated example user interface presented on the client device 130 in FIG. 4C includes motion restriction regions 410 through 413. The motion restriction regions 410 through 413 anchor a user's left and right index and middle fingers. As illustrated, the motion restriction regions 410 and 412 for anchoring the left and right middle fingers are positioned higher than the motion restriction regions 411 and 413 for anchoring the left and right index fingers, respectively. In addition, the centers of the motion restriction regions 410 and 412 as well as the centers of the motion restriction regions 411 and 413 are separated by an average distance between the tips of an adult's middle and index fingers. Furthermore, the motion restriction regions 410 and 411 and the motion restriction regions 412 and 413 are positioned such that the user's left and right hands are anchored to the left and right edges of the client device 130 and the other fingers are prevented from touching the touchscreen of the client device 130, and restricting the degrees of freedom of motion of the left wrist and arm.

The example user interfaces illustrated in FIGS. 4A through 4C require a user to anchor fingers from both hands to the touchscreen of the client device 130 to prevent both hands from moving and also to prevent free (i.e., non-anchored) fingers from making motions such as persisting spatial positioning data, recording information that may skew or improve a user's test performance. The example user interfaces illustrated in FIGS. 4A through 4C may be used in those tests to evaluate a user's memory or learning skills (e.g., present a sequence of letters and require the user to repeat the sequence of letters) and associated potential neurological deficit. For example, both of a user's hands are anchored during the prompt (e.g., display of the sequence of letters) to prevent the user from taking down any notes. One or both of the user's hands may be freed when the user is required to respond. The example user interfaces illustrated in FIGS. 4A through 4C may be used in those tests to evaluate particular motor skills (e.g., fast and slow muscle responses, motor coordination) and associated potential neurological deficit.

For example, since both hands must be in constant contact with the display device during the test, the user cannot use one hand to take notes, to hover fingers over areas of interest, or to provide additional inputs for the test (e.g., extra taps, drags, touches or other motions be tested). The motion restriction regions may be configured to anchor a user's fingers in a variety of arranged positions that are not necessary symmetrical positions as illustrated. As such, non-anchored fingers are prevented from participating in compensatory or performance enhancement data contributions.

FIGS. 5A through 5E each illustrate an example user interface for conducting self-administered tests, according to one embodiment. Unlike the examples illustrated in FIGS. 4A through 4C, the example user interfaces illustrated in FIGS. 5A through 5E requires a user to anchor one or more fingers of one hand to the touchscreen of the client device 130 in multiple motion restriction regions, while one or more fingers of the other hand are required to perform a task in one or more testing regions.

Figure 5A:
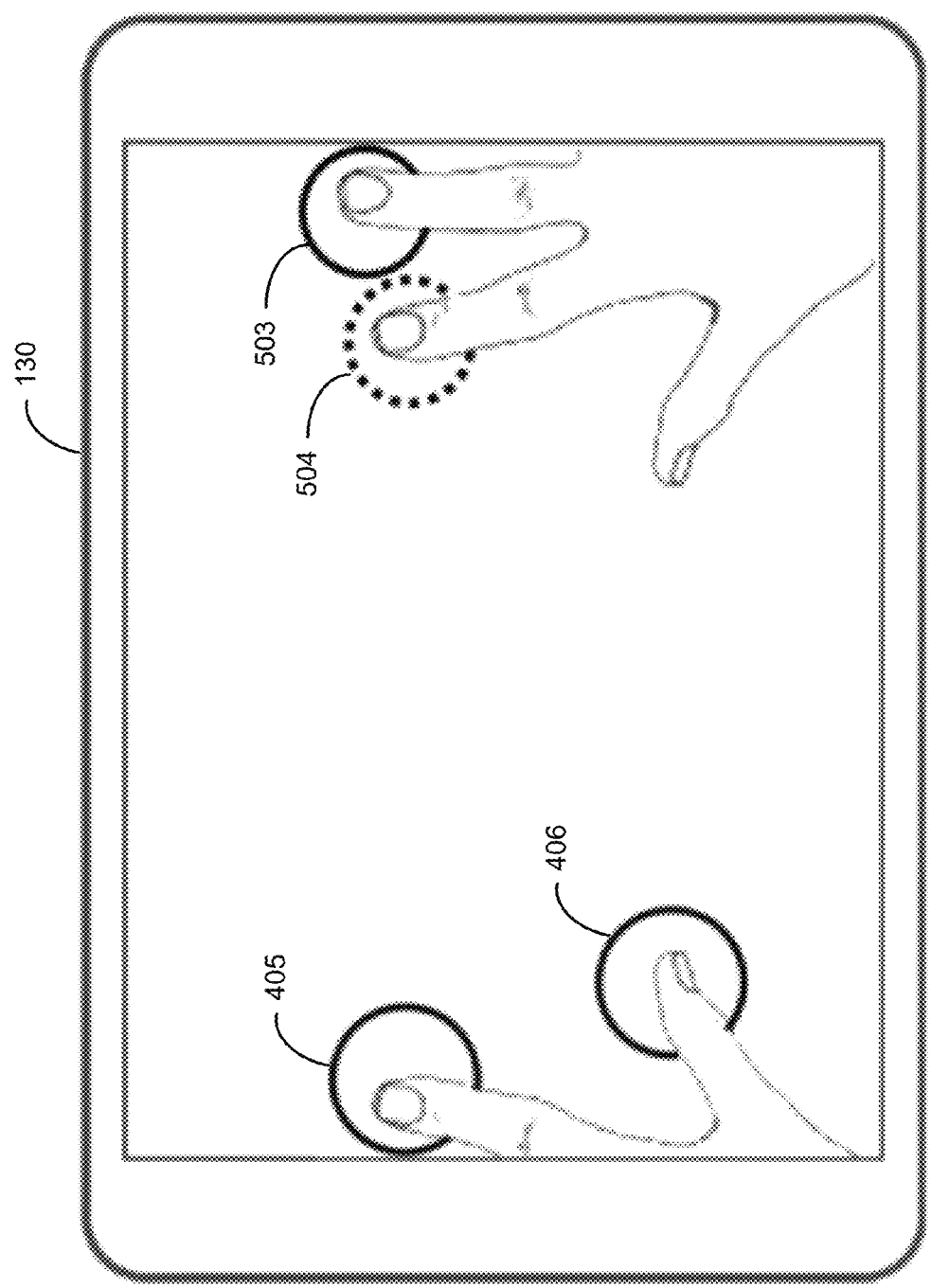
FIG. 5A illustrates an example user interface for conducting self-administered tests, according to one embodiment.

The illustrated example user interface presented on the client device 130 in FIG. 5A includes motion restriction regions 405, 406, and 503, and a testing region 504. The test region 504 is located on a first side of the touchscreen, for example here illustrated on the right side. The motion restriction regions 405 and 406 located on the opposing side of the touchscreen, here the left side, and are described in connection with FIG. 4B. The motion restriction region 503 anchors the user's right middle finger whereas the testing region 504 is configured for the user's right index finger to perform repetitive tasks such as tapping, making circular motions, etc., which are measured during the test to evaluate particular motor skills and associated potential neurological deficits. As illustrated, the motion restriction region 503 for anchoring the right middle finger is positioned higher than the testing region 504 for positioning the right index finger. In addition, the center of the motion restriction region 503 and the center of the testing region 504 are separated by an average distance between the tips of an adult's middle and index fingers (e.g., about 1.25"). Furthermore, the motion restriction region 503 and the testing region 504 are positioned such that the user's right hands are anchored to the right edge of the client device 130 and the right ring and pinky fingers are prevented from touching the touchscreen of the client device 130. In this arrangement, during the test the user is to tap the testing region 504 as many times as they can during the test, for example, for a duration of 30 seconds. Since the user's left hand is anchored to the display via their fingers being in contact with motion restriction regions 405 and 406, they cannot use fingers from their left hand to simultaneously tap on the testing region 405. Similarly because the right middle finger is anchored to motion restriction region 503, the user cannot use that finger (or the remaining fingers of the right hand) to tap as well. This ensures that the user can only tap with single finger (index finger, right hand) and so the test data is accurate and reliable. If the user were to lose contact with any of the motion restriction regions during the test, the test could be terminated and restarted, or the data inputs during such period when contact is lost may be indicated as being invalid.

Figure 5B:
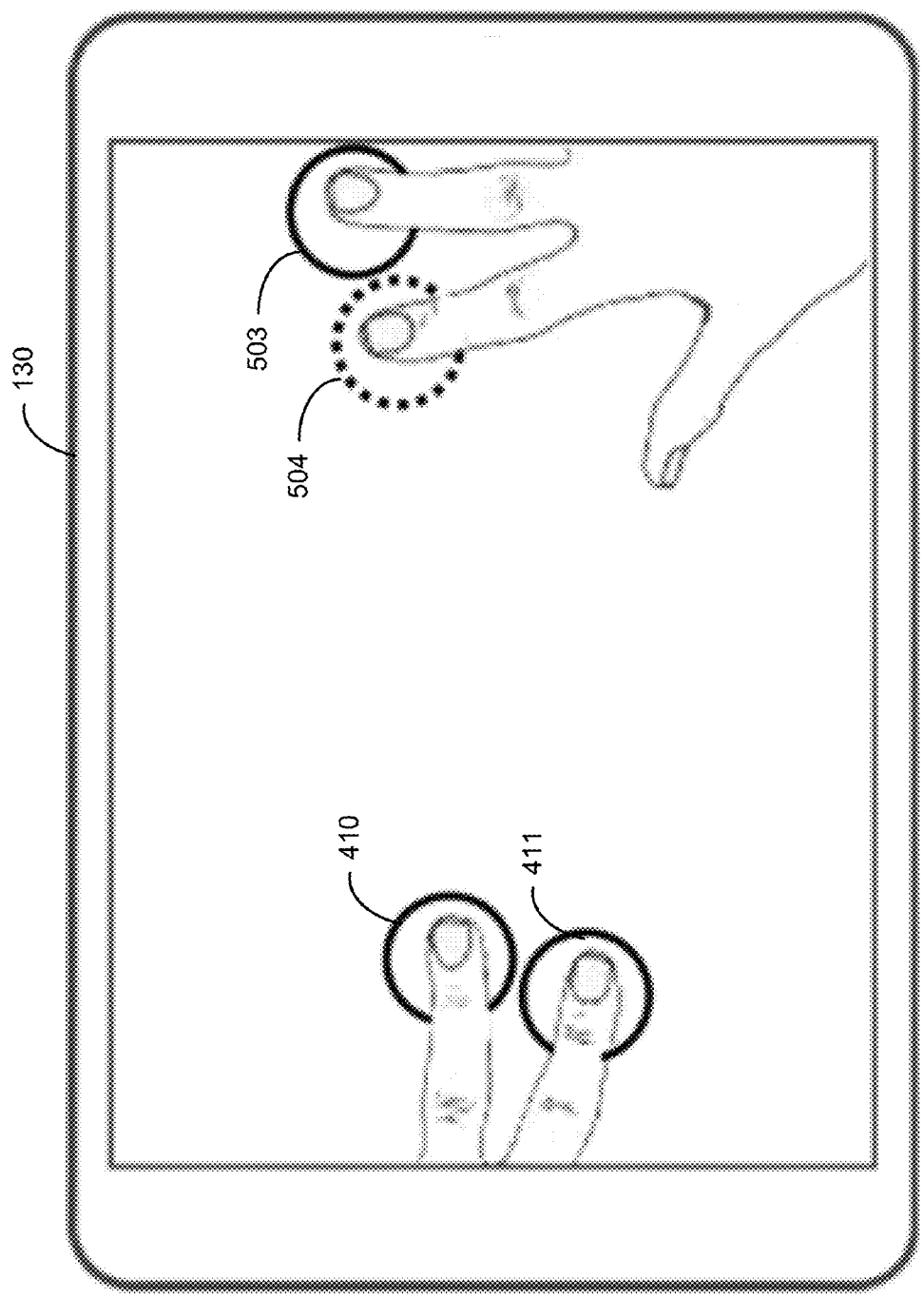
FIG. 5B illustrates an example user interface for conducting self-administered tests, according to one embodiment.
Figure 5C:
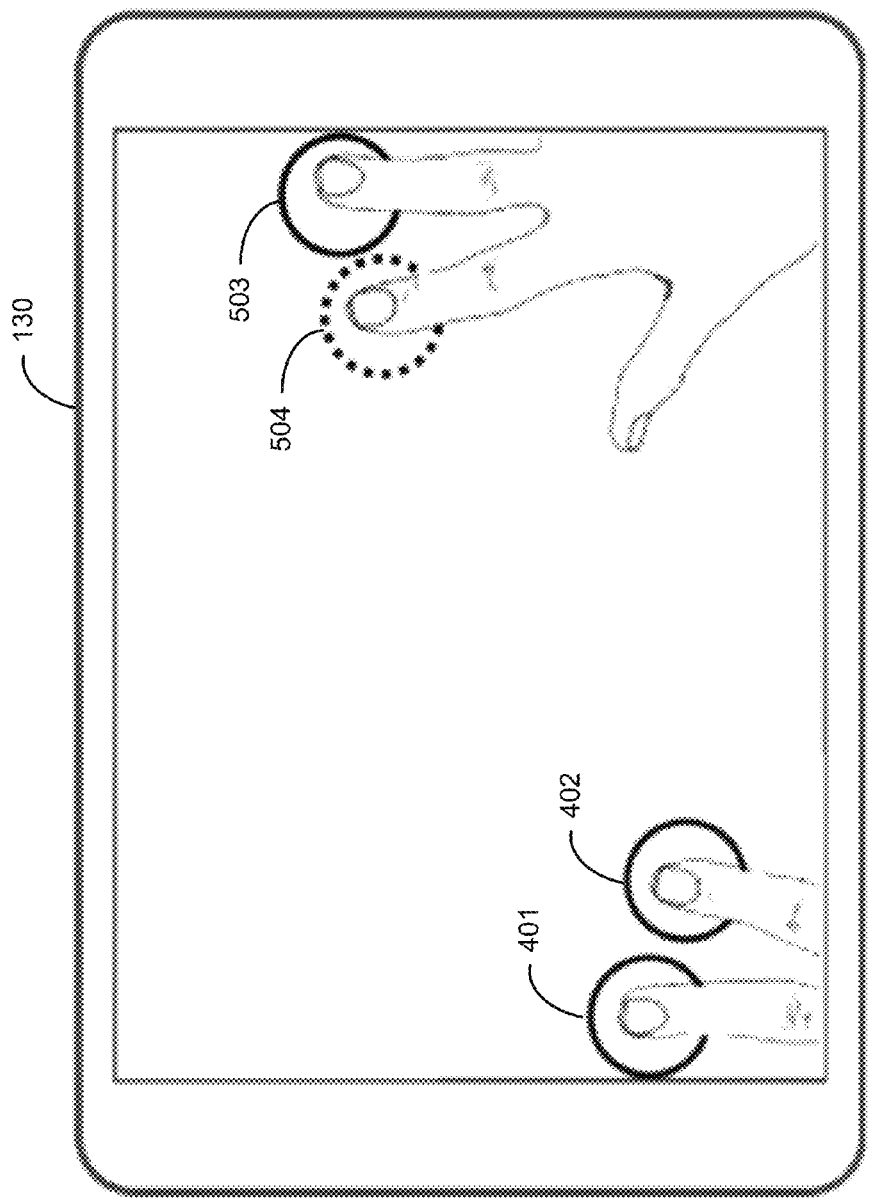
FIG. 5C illustrates an example user interface for conducting self-administered tests, according to one embodiment.
Figure 5D:
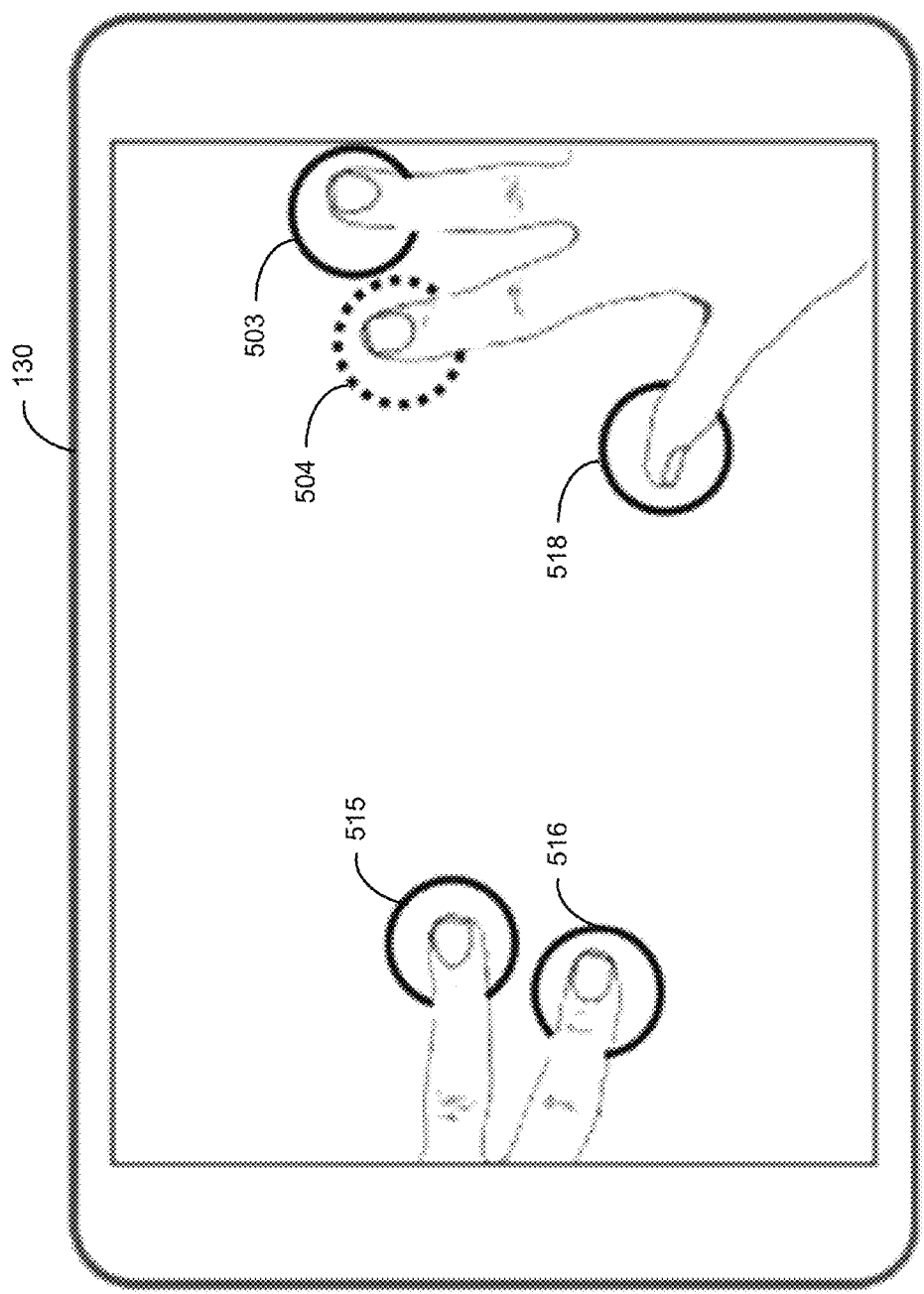
FIG. 5D illustrates an example user interface for conducting self-administered tests, according to one embodiment.

FIGS. 5B through 5D illustrate additional example user interfaces that are similar to the example user interface illustrated in FIG. 5A. The example user interface illustrated in FIG. 5B includes a motion restriction region 503 and a testing region 504 as described in connection with FIG. 5A and motion restriction regions 410 and 411 for anchoring a user's left middle and index fingers. The motion restriction regions 410 and 411 are described in connection with FIG. 4C.

The example user interface illustrated in FIG. 5C includes a motion restriction region 503 and a testing region 504 as described in connection with FIG. 5A and motion restriction regions 401 and 402 for anchoring a user's left middle and index fingers. The motion restriction regions 401 and 402 are described in connection with FIG. 4A. The example user interface illustrated in FIG. 5D includes a motion restriction region 503 and a testing region 504 as described in connection with FIG. 5A and motion restriction regions 410 and 411 for anchoring a user's left middle and index fingers as described in connection with FIG. 4C. In addition, the illustrated user interface includes a motion restriction region 518 for anchoring the user's right thumb to further restrict the user's right hand movement.

Figure 5E:
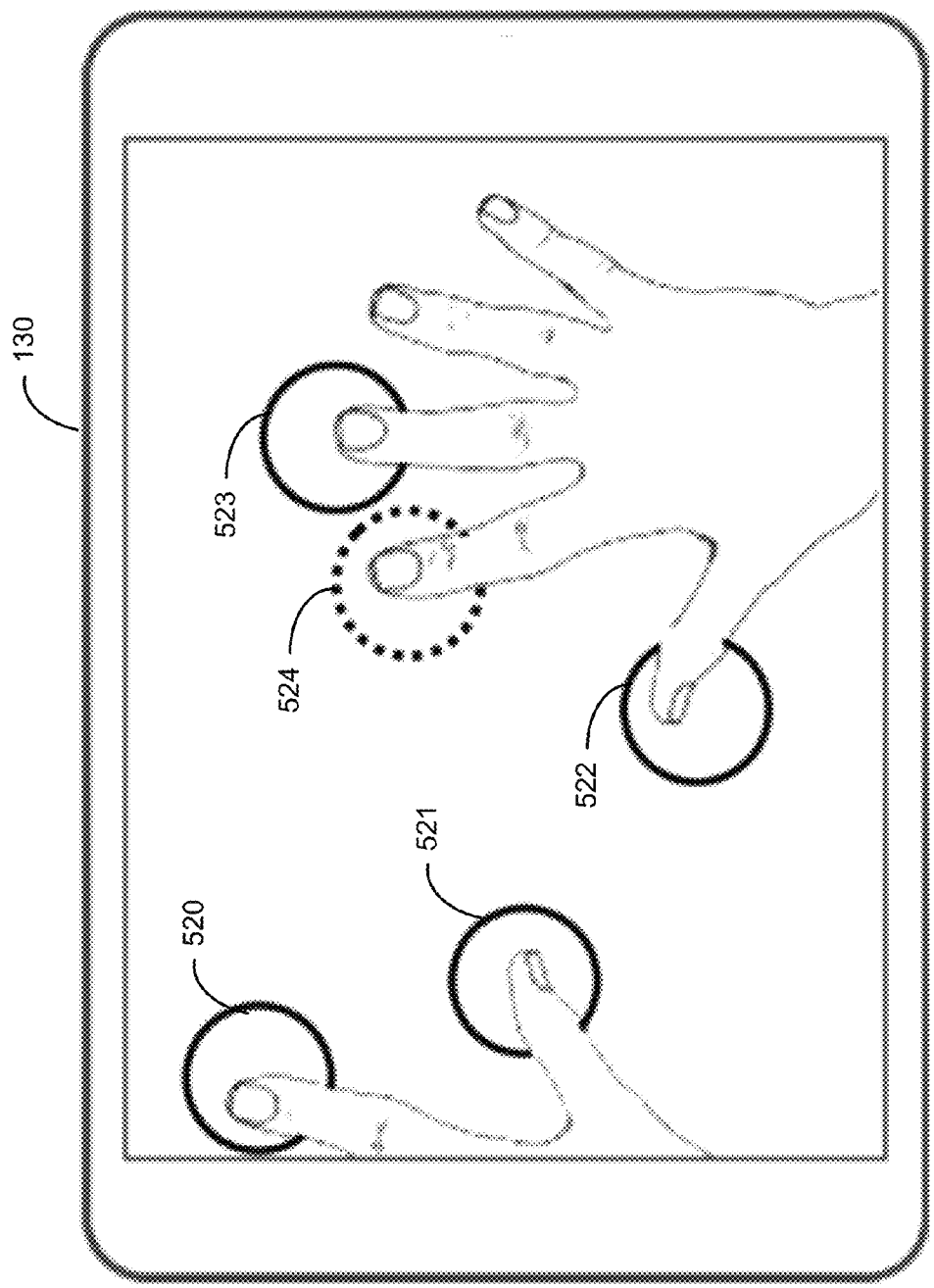
FIG. 5E illustrates an example user interface for conducting self-administered tests, according to one embodiment.

The illustrated example user interface presented on the client device 130 in FIG. 5E includes motion restriction regions 520 through 523 and a testing region 524. The motion restriction regions 520 and 521 are configured relatively similar to the motion restriction regions 405 and 406 as described in connection with FIG. 4B. The motion restriction regions 520 and 521 are positioned such that the user's left hand is anchored to the left edge and the user's left finger is anchored to the upper left corner of the client device 130 and the other fingers of the left hand are prevented from touching the touchscreen of the client device 130. The motion restriction regions 522 and 523 anchor the user's right thumb and middle finger, respectively, whereas the testing region 504 is configured for the user's right index finger to perform tasks such as tapping, making circular motions, etc. As illustrated, the motion restriction region 523 for anchoring the right middle finger is positioned higher than the testing region 524 for positioning the right index finger. In addition, the center of the motion restriction region 523 and the center of the testing region 524 are separated by an average distance between the tips of an adult's middle and index fingers. Furthermore, the motion restriction region 523 and the testing region 524 are positioned such that the user's right hands are anchored to the right half of the client device 130 and the right ring and pinky fingers can still touch the touchscreen of the client device 130.

All of the foregoing examples illustrated testing regions for the right hand; it should be apparent to those of skill in the art that in practice arrangement of motion testing regions may be utilized for the left hand as well, with complementary motion restriction regions, for example, by reflecting the above illustrated examples in vertical, medial axis of the touch-sensitive surface.

Example Use Cases

The following are examples of tests in which the use of motion restriction regions ensures that the motor skills or cognitive abilities being tested are accurately and reliably measured by preventing compensatory strategies or inputs.

Biometric or Psychometric Learning Test: In this type of test, the client device displays a list of stimuli (words, numbers, images) on the display device, or the stimuli are presented audibily (e.g., the words output from recorded or synthesized speech); the user is required to respond by orally repeating as many of the stimuli as they can after they are presented. During the test the user is instructed to anchor one or more fingers of both hands to the touchscreen of the client device. Anchoring fingers of both hands prevents the user from using his or her hands to capture data during the learning test, for example by writing down notes with the list of stimuli. During the test, if the anchored fingers are dislodged or moved outside the corresponding motion restriction regions even though they remain in contact with the touchscreen, the test is terminated and restarted. Alternatively, the test results (i.e., the responses to the test) are annotated to indicate that the user broke contact with the motion restriction regions during the test.

Visuospatial Learning Example: In this type of test, a user is presented a sequence of stimuli on the display device in a pattern of locations, and then the user is instructed to touch the display device's touchscreen at various locations according to the presented sequence. The user's fingers of both hands are required to be in contact with motion restriction regions as described above while the stimuli are initially presented on the client device to the user. Anchoring the fingers of both hands prevents the user from using one or more of their fingers to maintain a persistent reference to the displayed spatial locations (i.e., placing their hands on the display screen where the stimuli have been shown) or from capturing spatial locations on paper or another screen equivalent that could be used subsequently. During the presentation of the stimuli, if the anchored fingers are dislodged or moved outside the corresponding motion restriction regions even though they remain in contact with the touchscreen, the test is terminated and restarted. Alternatively, the test results (i.e., the responses to the test) are annotated to indicate that the user broke contact with the motion restriction regions during the test.

As a further example, a user is instructed to anchor one or more fingers of one hand to motion restriction regions on the touchscreen of the client device while the other hand is required to perform a given task. Anchoring the hand to the client device prevents the user from using the hand to record information that may influence the user's task performance or from contributing data to the target hands task performance. For example, a user uses the free hand to touch testing regions which is intended to be touched only by the hand that is designated for the user to use to perform the task. When the anchored fingers are dislodged or move outside the corresponding motion restriction regions even though they remain in contact with the touchscreen, the user disrupts the learning test.

Upon reading this disclosure, those of skill in the art will appreciate still additional alternative designs for a unified communication interface providing various communication services. Thus, while particular embodiments and applications of the present disclosure have been illustrated and described, it is to be understood that the embodiments are not limited to the precise construction and components disclosed herein and that various modifications, changes and variations which will be apparent to those skilled in the art may be made in the arrangement, operation and details of the method and apparatus of the present disclosure disclosed herein without departing from the spirit and scope of the disclosure as defined in the appended claims.

The invention claimed is:

1. A computer-implemented method, comprising:
configuring a touch-sensitive surface of a client device to present a computer-mediated, self-administered test to include a set of motion restriction regions and a user interface to receive a test input in response to the test, the set of motion restriction regions configured on the touch-sensitive surface to restrict motion inputs to the touch-sensitive surface during the test;
starting the computer mediated test on the client device, and receiving the motion inputs on the touch-sensitive surface and the test input via the user interface during the test;
determining whether one of the motion inputs on the touch-sensitive surface is a permitted input or a prohibited input in any of the motion restriction regions;
responsive to the motion input being a prohibited input, determining that the test input is invalid; and
responsive to the motion input being a permitted input, determining that the test input is valid.

2. The computer-implemented method of claim 1, wherein the set of motion restriction regions comprises a motion restriction region for anchoring a user's finger to the touch-sensitive surface.

3. The computer-implemented method of claim 1, wherein determining whether one of the user inputs on the touch-sensitive surface is a permitted input or a prohibited input in any of the set of motion restriction regions comprises:
receiving from the client device, motion data corresponding to the motion input, the motion data associated with a motion type, a location on the touch-sensitive surface, and time;
determining from the location of the motion data whether the user input is within a motion restriction region of the set of motion restriction regions; and
responsive to the location of the user input being within a motion restriction region, determining from the motion type of the motion data whether the user input is a permitted input or a prohibited input.

4. The computer-implemented method of claim 3, wherein the motion data comprises a finger-down event, a finger-up event, and a finger-move event.

5. The computer-implemented method of claim 4, wherein determining from the motion type of the motion data whether the user input is a permitted input or a prohibited input comprises:
registering a finger-down event in the motion restriction region prior to starting the test; and
determining that the user input is a prohibited input responsive to determining that the user input comprises a finger-up event in the motion restriction region.

6. The computer-implemented method of claim 1, further comprising terminating the self-administered test responsive to determining that the motion input being the prohibited input.

7. The computer-implemented method of claim 1, further comprising discarding the user input in the testing region responsive to determining the motion input being the prohibited input.

8. The computer-implemented method of claim 1, wherein the user interface is the touch-sensitive surface and the configuring the user interface to receive the test input comprises configuring the touch-sensitive surface to further include a testing region for receiving the test input.

9. The computer-implemented method of claim 8, wherein the testing region is located on a first side of the touch-sensitive surface, and wherein the set of motion restriction regions comprises a first motion restriction region located on the first side of the touch-sensitive surface, the first motion restriction region configured to anchor a user's finger to the touch-sensitive surface during the test.

10. The computer-implemented method of claim 8, wherein the testing region is located on a first side of the touch-sensitive surface, and wherein the set of motion restriction regions comprises a first motion restriction region located on the first side of the touch-sensitive surface and a second motion restriction region located on a second side of the touch-sensitive surface, wherein the second side opposes the first side and the first and second motion restriction regions are configured to anchor a user's first and second fingers to the touch-sensitive surface during the test.

11. The computer-implemented method of claim 8, wherein the set of motion restriction regions comprises a first motion restriction region located on the first side of the touch-sensitive surface and a second motion restriction region located on a second side of the touch-sensitive surface, wherein the second side opposing the first side, and the first and second motion restriction regions are configured to anchor a user's first and second fingers to the touch-sensitive surface during the test.

12. A non-transitory computer-readable storage medium storing executable computer instructions that, when executed by a hardware processor, perform steps comprising:
  configuring a touch-sensitive surface of a client device to present a computer-mediated, self-administered test to include a set of motion restriction regions and a user interface to receive a test input in response to the test, the set of motion restriction regions configured on the touch-sensitive surface to restrict motion inputs to the touch-sensitive surface during the test;
  starting the computer mediated test on the client device, and receiving the motion inputs on the touch-sensitive surface and the test input on the user interface during the test;
  determining whether one of the motion inputs on the touch-sensitive surface is a permitted input or a prohibited input in any of the motion restriction regions;
  responsive to the motion input being a prohibited input, determining that the test input is invalid; and
  responsive to the motion input being a permitted input, determining that the test input is valid.

13. The non-transitory computer-readable storage medium of claim 12, wherein the set of motion restriction regions comprises a motion restriction region for anchoring a user's finger to the touch-sensitive surface.

14. The non-transitory computer-readable storage medium of claim 12, wherein determining whether one of the user inputs on the touch-sensitive surface is a permitted input or a prohibited input in any of the set of motion restriction regions comprises:
  receiving from the client device, motion data corresponding to the motion input, the motion data associated with a motion type, a location on the touch-sensitive surface, and time;
  determining from the location of the motion data whether the user input is within a motion restriction region of the set of motion restriction regions; and
  responsive to the location of the user input being within a motion restriction region, determining from the motion type of the motion data whether the user input is a permitted input or a prohibited input.

15. The non-transitory computer-readable storage medium of claim 14, wherein the motion data comprises a finger-down event, a finger-up event, and a finger-move event.

16. The non-transitory computer-readable storage medium of claim 15, wherein determining from the motion type of the motion data whether the user input is a permitted input or a prohibited input comprises:
  registering a finger-down event in the motion restriction region prior to starting the test; and
  determining that the user input is a prohibited input responsive to determining that the user input comprises a finger-up event in the motion restriction region.

17. The non-transitory computer-readable storage medium of claim 12, further storing executable computer instructions configured to cause the hardware processor to further perform terminating the self-administered test responsive to determining that the motion input being the prohibited input.

18. The non-transitory computer-readable storage medium of claim 12, further storing executable computer instructions configured to cause the hardware processor to further perform discarding the user input in the testing region responsive to the motion input being the prohibited input.

19. The non-transitory computer-readable storage medium of claim 12, wherein the user interface is the touch-sensitive surface and the configuring the user interface to receive the test input comprises configuring the touch-sensitive surface to further include a testing region for receiving the test input.

20. The non-transitory computer-readable storage medium of claim 19, wherein the testing region is located on a first side of the touch-sensitive surface, and wherein the set of motion restriction regions comprises a first motion restriction region located on the first side of the touch-sensitive surface and a second motion restriction region located on a second side of the touch-sensitive surface, wherein the second side opposes the first side and the first and second motion restriction regions are configured to anchor a user's first and second fingers to the touch-sensitive surface during the test.

* * * * *